United States Patent
Infante Martínez et al.

(10) Patent No.: US 7,015,019 B2
(45) Date of Patent: Mar. 21, 2006

(54) 1-O-L-ARGINYL ESTER 3-O-MONOACYL GLYCERIDES AND 1-O-L-ARGINYL ESTER 2,3-O-DIACYL GLYCERIDES TYPE SURFACE ACTIVE AGENTS

(75) Inventors: M$^a$ Rosa Infante Martínez, Barcelona (ES); M$^a$ Lourdes Pérez Muñoz, Barcelona (ES); Carmen Moran Badenas, Barcelona (ES); Pere Clapes Saborit, Barcelona (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 559 days.

(21) Appl. No.: 10/214,402

(22) Filed: Aug. 7, 2002

(65) Prior Publication Data

US 2003/0044984 A1 Mar. 6, 2003

Related U.S. Application Data

(63) Continuation of application No. PCT/ES01/00039, filed on Feb. 8, 2001.

(30) Foreign Application Priority Data

Feb. 11, 2000 (ES) .......................................... 200000319

(51) Int. Cl.
*C12P 13/10* (2006.01)
*C12N 5/00* (2006.01)
*A01N 25/26* (2006.01)
*C07C 229/00* (2006.01)

(52) U.S. Cl. ....................... 435/114; 424/417; 424/420; 435/458; 554/105

(58) Field of Classification Search ................ 435/114, 435/458; 424/117, 420, 417; 554/105
See application file for complete search history.

(56) References Cited

U.S. PATENT DOCUMENTS 3,985,722 A * 10/1976 Yoshida et al. ............. 530/360
5,780,658 A * 7/1998 Martinez-Pardo et al. .... 554/51

FOREIGN PATENT DOCUMENTS

| | | |
|---|---|---|
| EP | 0320976 | 12/1988 |
| ES | 512643 | 5/1982 |
| ES | 2092958 | 1/1995 |
| ES | 9900739 | 4/1999 |
| ES | 2130980 | 4/2000 |
| WO | PCT/ES96/00026 | 1/1996 |
| WO | WO9621642 | 7/1996 |

OTHER PUBLICATIONS

Maugard et al, Kinetic study of chemoselective acylation of amino–alditol by immobilized lipase in organic solvent: effect of substrate ionization; (1998) 177–183.
R. Yoshida et al; Surfactants derived from amino acids, vol. 25, 1976.
K. Kawashiro et al, Bioeng. 42, (1993) 309–314.
J.H. Fendler, Membrane Mimetic Chemistry (1989).
Yun–peng Zhu et al, J. Am. Oil. Chem. Soc., 69:6269 (1992).
Frank D. Gunstone et al, Lipid Technologies and Applications (1997).
Takehara, M. (1989), Colloids and Surfaces, 38:149.
C. Selve, (1992) J. Chem. Res. 22:401.
K. Sagawa et al, New Powder Material Prepared from Amino Acid, (1986) 429–448.
M.R. Infante et al, Lipopeptidic Surfactants, JAOCS, vol. 69, No. 7 (Jul. 1992).
J. Molinero et al, Synthesis and Properties of N$^\alpha$ Lauroyl–L–Arginine JAOCS, vol. 65, no 6 (1988).
C. Solans, et al, Progress in Colloid & Polymer Science 81:144–150 (1990).
L. Perez et al, Langmuir, vol. 12, No. 22, pp. 5296–5301, 1996.
P. Clapes et al, Enzymatic Synthesis of Arginine–Based Cationic Surfactants, (1998) 335–343.
K. Larsson, Lipids—Molecular Organization, Physical Functions and Technical Applications (1994).
S. E. Friberg et al, Food Emulsions, (1997).
R. Valivety et al, (1998) J. Surf. Deterg. 1 177–185.
D. Cantacuzene, Tetrahedron Letters 28, 5153–5156, 1987.
H. Kise et al (1987), Biotechnol. Lett. 9 543–548.
Y.V. Mitin et al, (1997) Biotech. and Bioeng. 54, 287).
M. Bodanszky et al, The Practice of Peptide Synthesis, (1984).

* cited by examiner

*Primary Examiner*—Herbert J. Lilling
(74) *Attorney, Agent, or Firm*—Klauber & Jackson

(57) ABSTRACT

This invention refers to new surface-active compounds derived from arginine of the mono and diacylglyceride type according to the general formula (I) designed to act as surface agents with antimicrobial activity. The variations in the activity will depend on the number of fatty chains and their length. The purification of the intermediate and final products is achieved by means of liquid/liquid, liquid/solid extractions, crystallizations, ion-exchange chromatography and reverse-phase HPLC.

18 Claims, No Drawings

1-O-L-ARGINYL ESTER 3-O-MONOACYL GLYCERIDES AND 1-O-L-ARGINYL ESTER 2,3-O-DIACYL GLYCERIDES TYPE SURFACE ACTIVE AGENTS

This application is a continuation of international application number PCT ES01/00039, filed Feb. 8, 2001.

INTRODUCTION

The surfactants are versatile widely-used organic molecules that contain two functional groups with opposite characteristics: a hydrophilic group (soluble in water) and an insoluble hydrophobic group. Current European requirements, both with respect to the profitability of processes as well as ecological concerns, make it absolutely necessary to undertake research on new products capable of protecting the environment and the quality of life as well as alternatives that will improve production processes. One of the strategies existing at the present time in order to obtain ecologically-acceptable surfactants is the preparation of molecules with a molecular structure mimetic of the natural surface-active compounds: lipoamino acids, phospholipids and glycerolipids (J. H. Fendler, 1989, "*Membrane Mimetic Chemistry*, John Wiley & Son). Since 1984, the team led by Dr. Infante, a ground-breaker in this research in Spain, has been interested in the synthesis, study and development of lipoamino acids (amides, esters and acyls) with highly different structures and ionic characteristics, characterized by containing an amino acid or peptide in their hydrophilic or polar part and, in their hydrophobic or apolar part, one or more fatty chains condensed from the amino acid, on account of their α-amino or terminal carboxyl functions. In addition, the glycerolipids, particularly the mono and diacylglycerides (known as monodiacylglycerides), constitute at the present time, thanks to their excellent emulsifying and carrier properties (Zhu, Y., Masuyama, A., Kirito, Y., Okahara, M., Rosen, M. J., 1992, *J. Am. Oil. Chem. Soc.*, 69:6269), 75% of the emulsifiers used in the food industry, the monoacylglicerides being the most important among them on account of their greater functionality and more competitive nature. Within this group, the most extensively studied and widely used compounds are the alkyl esters of glycerol, as they are obtained easily by means of the glycerolization of triacylglicerides or by esterification of the glycerol by means of fatty acids (*Lipid Technologies and Applications*, 1997, Ed. Gunstone, F. D., Padley, F. B., New York). The monoacylglicerides are compounds with very low solubility in water, for which reason they are generally added to formulas together with other emulsifiers of a more polar nature The purpose of this invention is the synthesis of a new family of monoacylglycerides and diacylglycerides derived from arginine, similar to the classical monoacylglycerides but with characteristics of a more hydrophilic nature. These surfactants are made up by a central glycerol backbone that links the hydrophobic part formed by one or two fatty acid chains of a variable length to the hydrophilic part formed by the amino acid arginine or acetyl-arginine linked to the glycerol by its terminal hydroxyl through an ester bond. These new structures provide certain advantages over the conventional monodiacylglycerides previously described: a) the introduction of the arginine as the polar part of the amphiphilic molecule will increase their solubility in an aqueous solution, and will improve their surface-active properties in water, b) the presence of arginine will provide cationic characteristics to the surfactant and, thus, compounds will be obtained with antimicrobial activity and c) depending on the nature and number of the hydrophobic chains, it is to be expected that, in water, the new molecules will aggregate spontaneously forming cubosomes and/or liposomes useful for the transport and liberation of biomolecules.

STATE OF THE TECHNIQUE

The surfactants derived from amino acids are compounds of great interest due to their multifunctionality and innocuity (Takehara, M. 1989, *Colloids and Surfaces*, 38:149; Selve, C., Mansuy, L., Allouch, M., 1992, *J. Chem. Res.* 22:401). These characteristics are the ones responsible for the fact that in the last few years the synthesis and the study of the properties of a wide range of surfactants of this type, of an ionic, cationic, nonionic and amphoteric nature, have been carried out (Takehara, M. 1989, *Colloids and Surfaces*, 38:149; Sagawa, K., Yokota, H., Ueno, I., Miyosi, T., Takehara, M., 1986 *XIV Congreso IFSCC*). Along these lines, our team, by means of chemical and enzymatic methodologies, has synthesized monocatenary, dicatenary lipoamino acids and geminal compounds of a highly varied structure wherein the fatty chain was linked to the amino acid by acyl, ester or amide bonds. This study has given rise to a large number of patents and publications (ES 9500061 (1995); PI 9500027 (1995); PCT/ES96/00026 (1996); ES 9700520 (1997); ES 9900739 (1999); M. R. Infante, J. Molinero, P. Erra, (1992), *JAOCS*, vol. 69, no. 7; J. Molinero, M. R. Julia, P. Erra, M. Robert, M. R. Infante, 1988, *JAOCS*, vol. 65, no. 6; C. Solans, M. A. Pés, N. Azemar, M. R. Infante, 1990, *Prog. Colloid Polym* Sci 81, pp. 144–150; L. Pérez, J. L. Torres, A. Manresa, C. Solans, M. R. Infante, 1996, *Langmuir*, 12(22) pp. 5296–5301, Clapés, P., Morán, C., Infante, M. R. (1999) *Biotechnol. Bioeng.* 63 3 pp. 333–343).

With respect to the monodiacylglycerides, the relevant bibliography provides a detailed description of their properties and applications (K. Larsson, 1994, "*Lipids: Molecular Organization, Physical Functions and Technical Applications*" The Oily Press LTD). These properties become noticeably modified when the free hydroxyl end of the molecule is functionalized with organic acids of the lactic, citric and acetic acid type ("*Food Emulsions*", 1997, Ed. by Stig E. Friberg and K. Larsson).

The synthesis of mono and diacylglycerides derived from arginine, the object of this invention, requires the prior obtaining of the derivatives of the 1-O-L-arginyl glycerol ester type. The relevant bibliography describes the synthesis of these intermediates by using chemical catalysts. Valivety et al. (Valivety, R., Gill, I.S., Vulfson, E. N., 1998, *J. Surf. Deterg.* 1 177–185) prepared a number of compounds of the 1-O-L-aminoacyl glycerol esters type from $N^\alpha$-Z-amino acids and glycerol in the presence of $BF_3$-etherate. However, in no case are derivatives of arginine involved.

Although the obtaining of glyceryl esters with N-protected amino acids as starting materials has scarcely been developed, there are numerous publications based on the enzymatic synthesis of ester bonds (Cantacuzene, D., Guerreiro, C., 1987, *Tetrahedron Letters* 28, 5153–5156; Kawashiro, K., Inhizaki, H., Sugiyama, S., Hayashi, H., 1993, *Biotechnol. Bioeng.* 42, 309–314; Kise, H., Hayakawa, A., Noritomi, H., 1987, *Biotechnol. Lett.* 9 543–548). Mitin et al. (Mitin, Y. V., Braun, K., Kuhl, P., 1997, *Biotech. and Bioeng.* 54, 287) describe how the glyceryl esters of N-protected amino acids are obtained for use in the synthesis of peptides, although no examples of arginine derivatives are found in the relevant literature. With respect to the acylation of the hydroxyl groups of the glycerol, we have found the use of enzymes of the lipase type described (Valivety, R., Gill, I. S., Vulfson, E. N., 1998, *J. Surf. Deterg.* 1 177–185).

The principal novelties of this invention are the combination in a single molecule of surfactants of the mono and diacylglyceride type and surfactants derived from arginine, as well as the use of enzymes as substitutes for conventional chemical catalysts.

DESCRIPTION OF THE INVENTION

This invention refers to a new family of surfactants as well as to the procedures for the synthesis of these compounds. The structural formula of these compounds is shown below (I).

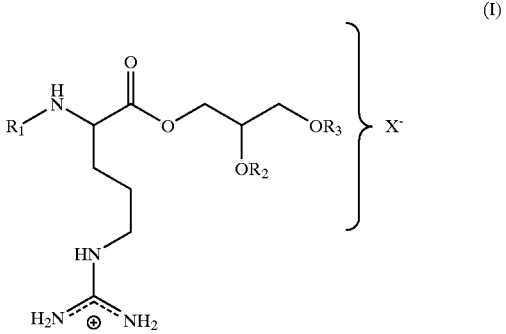

wherein:
$R_1$ can be a hydrogen or an acetyl group (Ac);
$R_2$ and $R_3$ can be a hydrogen or a straight chain, preferably a long one, either saturated or unsaturated; $R_2$ and $R_3$ can be selected from a group of straight chains of 8, 9, 10, 12, 14, 16 or 18 carbon atoms, either saturated or unsaturated, pure or mixtures thereof, and
said surfactants aggregate spontaneously in water forming cubosomes and/or liposomes.

The starting materials can be:
N-α protected derivatives of arginine, of a technical quality or specifically N-acetyl-arginine
Glycerol
Saturated or unsaturated straight fatty acids, esters or chlorides of different lengths
Technical quality chemical catalysts
Technical quality proteases and lipases There will be a variation in the molecules as to the number of alkyl chains (1 or 2), their degree of unsaturation and their length, which will give rise to compounds with a different behavior in their absorption, autoaggregation and biological properties. Because of the renewable and innocuous nature of the raw materials used, it should be expected that these compounds will not be dangerous, either from a biological or an environmental point of view. The use of the acetyl group as the protecting group for the amino function of the arginine makes it possible to avoid possible secondary reactions of the Maillard type without altering the biocompatible nature of the final products obtained. According to the process of the present invention the condensation of the glycerol with the N-α protected arginine takes place in a regioselective manner in the α position of the N-α protected derivative. The process also takes place in a regioselective manner in 1(3) position of the glycerol.

These compounds are obtained by chemical and enzymatic methodologies. The stages involved in each of the procedures are described below:

A) Chemical procedure: the chemical synthesis of these compounds takes place in three stages:
1) Formation of the $N^\alpha$-protected derivatives of arginine, 1-O-N-(prot)-arginyl-sn-glycerol ester (which will be referred to as 00R(prot). The starting materials are glycerol, L-arginine protected by the α-amino group and $BF_3$-etherate as the catalyst of the esterification reaction.
2) Formation of the $N^\alpha$-protected derivatives 1-O-arginyl ester 3-O-monoacylglycerides or 1-O-arginyl ester 2,3-O-diacylglycerides (which will be referred to as nnR (prot). The reaction takes place starting with 00R(prot) using straight fatty acid chlorides with 8 to 18 carbon atoms as acylating agents in a pyridine solution.
3) If appropriate, the formation of 1-O-arginyl ester 3-O-monoacylglycerides or 1-O-arginyl ester 2,3-O-diacylglycerides (which will be referred to as nnR) by means of a catalytic hydrogenation in Pd/C or an acidolysis.

B) Enzymatic procedure: the enzymatic synthesis is performed in three stages.
1) Obtaining of the 00R (prot). Condensation reaction of the glycerol with the carboxyl/ester group of the $N^\alpha$-protected arginine, using a hydrolytic enzyme, proteases or lipases preferably, as the catalyst, in a solvent-free solution with a certain percentage of water.
2) Obtaining of the nnR (prot). Acylation reaction of the free hydroxyl group(s) of the 00R(prot) with free fatty acids or esters of these acids, using a lipase as catalyst. The reaction takes place in a solvent-free solution in the presence of a small percentage of water in order to activate the enzyme. In the event acetyl-arginine is used as the protecting group, the final product, nnR(acetyl), will not be subjected to the following stage.
3) Obtaining of the nnR. If appropriate, elimination of the $N^\alpha$-protecting group of the mono or diacyl glyceride amino acid derivative by using routine conventional techniques in peptide synthesis (hydrogenation, acid treatment or β-elimination catalyzed by bases).

The present invention refers to new surface-active compounds derived from arginine of the mono and diacylglyceride type designed to act as surface agents with antimicrobial activity. The variations in the activity will depend on the number of fatty chains and their length.

The purification of the intermediate and final products is performed by means of liquid/liquid, liquid/solid extractions, crystallizations, ion-exchange chromatography and reverse-phase HPLC.

In a particular embodiment of the invention the progress of the reaction is followed by means of analysis by high-performance liquid chromatography, with a column of the propyl cyan and $C_{18}$ type, using water and acetonitrile as eluents. Among the lipases, preferably immobilized *Rhizomucor miehi* lipase and/or immobilized *Candida antarctica* lipase are used.

SYNTHESIS

As an illustration, which should not be understood to limit the procedure, an example is given below showing the obtention of a surfactant of the diacyl glycerol ester type with 8-carbon-atom fatty chains by means of a chemical process (88R) and of another of the monoacyl glycerol ester type with a 12-carbon-atom fatty chain through an enzymatic process (120 R). In both cases the amino acid used is arginine, and the compound is obtained in the form of a hydrochloride salt.

A) Chemical procedure

The compound is prepared in 3 stages as previously mentioned:
1) Preparation of the 00R(Z). A 0.8–1.2 Molar solution of Z-Arg-OH in glycerol is prepared. 10% in volume of DMF is added and is heated to a temperature of between 45–60° C. Afterwards, 5% in volume of $BF_3$-etherate is slowly added and the reaction is left for 5 hours. The solution is brought to pH 6–6.5 by means of the addition of $NaHCO_3$. The product is isolated by means of an ion-exchange column or by preparative-scale liquid chromatography in reverse phase (HPLC).

2) Preparation of 88R(Z). A solution in the range of 0.8–1.1 Molar of 00R(Z) is prepared to which catalytic amounts of an organic tertiary base are added (dimethyl amino pyridine, DMAP). Octyl chloride in a 2.5–3 Molar concentration is slowly added to this mixture. The reaction mixture is continuously stirred for 4–6 hours at a temperature of between 15–25° C. Afterwards, the solvent is eliminated under a vacuum and the mixture is purified by means of the MPLC or preparative-scale HPLC technique.

3) Preparation of 88R. The third stage consists of the removal of the protection of the α-amino group of the arginine by means of catalytic hydrogenation in a methanol solution using Pd/C and under atmospheric pressure during 4–6 hours. The product thus obtained is dissolved in water/HCl and is freeze-dried in order to obtain the compounds in the form of dihydrochloride salts.

B) Enzymatic procedure

As mentioned in the description, the process consists of three stages:

1) Preparation of the 00R(Boc) hydrochloride. In a reactor with an airtight closure the tert-butyloxycarbonyl arginine (1 eq) is dissolved in glycerol (5 eq) containing 10% of a 0.1 M pH 8.2 Boric/NaOH solution. The homogenization of the solution takes place by means of magnetic stirring. The protease papain is added to the solution (1.7 U/g of solid; 1 unit (U) of activity in this case corresponds to the amount of enzyme that hydrolyzes 1 $\mu$mol of benzoyl arginine ester per minute at pH 6.2 and 25° C. The reaction mixture is kept under an inert atmosphere and is continuously stirred by a back-and-forth movement (200 rpm) or equivalent and is thermostated at 50° C. in a water bath. The reaction is monitored by a high-performance liquid chromatography (HPLC) in reverse phase until all of the tert-butyloxycarbonyl arginine methyl ester has been consumed; approximately 48 hours. The yield at this point, and by HPLC, is 72%. An equal volume of a 4:1 methanol/acetic acid mixture is then added to the reaction solution and is filtered through a celite bed in order to separate the enzyme from the reaction solution with the product. The previously-evaporated filtrate is dissolved in water and is absorbed on a combined 1:1 celite/active carbon resin. In the initial stage the selective elution of the glycerol present in the solution takes place through treatment with water. Immediately afterwards, the 1-tert-butyloxycarbonyl arginine-sn-glycerol is eluted through treatment with a 1:1.2 methanol/water mixture. Following evaporation and freeze-drying, a white solid is obtained which is identified by mass spectrometry and proton and carbon nuclear magnetic resonance. The final yield is 55%.

2) Preparation of the 120R(Boc) hydrochloride. The commercial preparation Novozym 435, *Candida Antarctica* lipase B. commercialized by Novo Nordisk, is added to an open reactor containing 00R(Boc) (1 eq) and lauric acid (2 eq) at 55° C. containing 4% (w/w) of water, with the solution being continuously stirred and thermostated at 55° C. The reaction is monitored by high-performance liquid chromatography (HPLC) in reverse phase until all of the 1-tert-butyloxycarbonyl arginine-sn-glycerol has been consumed; approximately 72 hours. The yield at this point, and by HPLC, is 65%. Afterwards, an equal volume of an 80:19:1 acetonitrile/water/acetic acid mixture is added to the reaction solution and is filtered in order to separate the support containing the enzyme from the reaction solution with the product. The final product is obtained by means of conventional techniques of crystallization and/or chromatography.

3) Obtaining of 120R dihydrochloride. Once the 120R (Boc) hydrochloride has been purified, the protection is removed from the amine function. The tert-butyloxycarbonyl is eliminated by means of acid treatment with trifluoroacetic acid (M. Bodansky, A. Bodansky, The Practice of Peptide Synthesis. Springer-Verlag (Heidelberg) 1984).

The critical micellar concentration of the compounds is evaluated by conventional techniques, as this parameter indicates the surface activity of the surfactants in an aqueous solution. Likewise, the antimicrobial activity is determined on the basis of the minimum inhibitory concentration (MIC) values expressed in $\mu$g/mL. These parameters are indicated as an example in table 1 for one of the compounds claimed in this patent.

TABLE 1

| | CMC and antimicrobial activity of the surfactant 88R | | | | | |
|---|---|---|---|---|---|---|
| CMC | | MIC ($\mu$g/mL) | | | | |
| Compound | M (25° C.) | 1 | 2 | 3 | 4 | 5 |
| | | 6 | 7 | 8 | 9 | |
| 88R | $6.3 \times 10^{-3}$ | 64 | 16 | 32 | 4 | 32 |
| | | 16 | 32 | 16 | | |

1. *Pseudomonas aeruginosa* 47T2
2. *Streptococcus faecalis*
3. *Proteus mirabilis*
4. *Escherichia coli*
5. *Candida tropicalis*
6. *Candida lipolitica*
7. *Staphilococcus aureus*
8. *Bacillus cereus*
9. *Bacillus pumillus*

What is claimed is:

1. Cationic surfactants of the 1-O-L-arginyl ester 3-O-monoacyl glycerides and 1-O-L-arginyl ester 2,3-O-diacyl glycerides type as antimicrobial agents with high surface activity having the general formula:

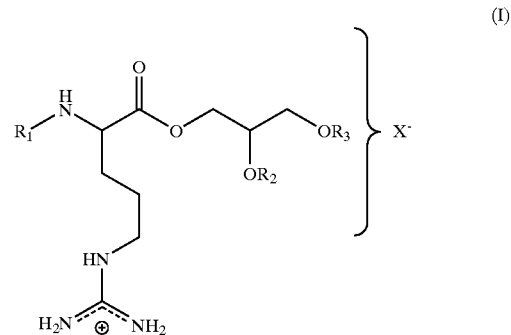

wherein:

R$_1$ can be a hydrogen or an acetyl group;

R$_2$ and R$_3$ can be a hydrogen or a straight chain, preferably long, either saturated or unsaturated; R$_2$ and R$_3$ can be selected from a group of straight chains of 8, 9, 10, 12, 14, 16 and 18 carbon atoms, either saturated or unsaturated, pure or mixtures thereof and said surfactants aggregate spontaneously in water forming cubosomes and/or liposomes wherein X is chloride.

2. Chemical or enzymatic process for obtaining surfactants having a general formula according to claim 1, comprising the following stages:

a first stage of formation of 1-O-N-(prot)-arginyl-sn-glycerol ester, 00R(prot), a second stage of formation of 1-O-N-(prot)-arginyl-3-O-monoacyl-sn-glycerol ester, n0R(prot) or 1-O-N-(prot)-arginyl-2,3-O-diacyl-sn-glycerol ester, nnR(prot), elimination of the N-α protecting group of the mono or diacyl glyceride arginine in order to obtain 1-O-arginyl-3-O-monoacyl-sn-glycerol ester, n0R or 1-O-arginyl-2,3-O-diacyl-sn-glycerol ester, nnR.

3. A process according to claim 2 wherein as starting compounds pure L-arginine or its racemic mixtures are used.

4. A process according to claim 2 wherein the acetyl (Ac), benzyloxycarbonyl (Z) and tert-butyloxycarbonyl (Boc) groups are used as the groups protecting the α-amino function of the arginine.

5. A process according to claim 2 wherein in the first stage of the chemical process the 1-O-N-(prot)-arginyl-sn-glycerol ester compounds from N-protected L-arginine and glycerol, are obtained by using $BF_3$ as the chemical catalyst of the reaction.

6. A process according to claim 2 wherein in the first stage of the enzymatic process the 1-O-N-(prot)-arginyl-sn-glycerol ester compounds are obtained from N-α protected arginine and glycerol by means of the catalysis of a hydrolytic enzyme in solvent-free solutions with a percentage of water.

7. A process according to any of claims 2, 5 or 6, wherein pure glycerol is used in order to obtain 1-O-N-(prot)-arginyl- sn-glycerol ester.

8. A process according to any of claims 2, 5 or 6, wherein the condensation of the glycerol with the N-α protected arginine takes place in a regioselective manner in the α position of the N-α protected derivative.

9. A process according to any of claims 2, 5 or 6, wherein the condensation of the glycerol with the N-α protected arginine takes place in a regioselective manner in 1(3) position of the glycerol.

10. A process according to claim 2, wherein the second stage of the chemical comprises the acylation of the free hydroxyl groups of 1-O-N-(prot)-arginyl-sn-glycerol ester in a pyridine solution.

11. A process according to claim 2 or 10 wherein chlorides of fatty acids with a straight chain of 8, 9, 10, 12, 14, 16 or 18 carbon atoms, either saturated or unsaturated are used in the acylation reaction of the free hydroxyl groups of 1-O-N-(prot)arginyl-sn-glycerol ester.

12. A process according to claim 2 wherein the second stage of the enzymatic process, corresponding to the acylation reaction of the acid or fatty acid ester with the free hydroxyl groups of the 1-O-N-(prot)-arginyl-sn-glycerol ester derivative, takes place by means of the mixture of both compounds without the need for a solvent.

13. A process according to claim 2 or 12 wherein fatty acids or fatty acid esters with a straight chain of 8, 9, 10, 12, 14, 16 or 18 carbon atoms, saturated or unsaturated are used, in the acylation reaction of the free hydroxyl groups of 1-O-N-(prot)-arginyl-sn-glycerol ester.

14. A process according to claim 2 or 13 wherein hydrolytic enzymes of the lipase type are used as biocatalysts of the acylation reaction of the free hydroxyl groups of 1-O-N-(prot)-arginyl-sn-glycerol ester.

15. A process according to claim 2 wherein the elimination of the protection of the α-amino group of the arginine is carried out either by catalytic hydrogenation with Pd/C or through acidolysis.

16. A process according to claim 2 that is followed by means of analysis by high-performance liquid chromatography, with a column of the propyl cyan and $C_{18}$ type, using water and acetonitrile as eluents.

17. A process according to claim 6, wherein the hydrolytic enzyme is selected from the group consisting of proteases and lipases.

18. A process according to claim 14 wherein the lipase is selected from the group consisting of immobilized *Rhizomucor miehi* lipase, immobilized *Candida antarctica* lipase.

* * * * *